United States Patent
Rashidi (10) Patent No.: US 10,143,516 B2
(45) Date of Patent: Dec. 4, 2018

(54) ELECTROPHYSIOLOGY/ABLATION CATHETER HAVING LARIAT CONFIGURATION OF VARIABLE RADIUS

(71) Applicant: St. Jude Medical, Atrial Fibrillation Division, Inc., St. Paul, MN (US)

(72) Inventor: Rassoll Rashidi, Lakewood, OH (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 0 days.

(21) Appl. No.: 14/311,515

(22) Filed: Jun. 23, 2014

(65) Prior Publication Data

US 2014/0364845 A1    Dec. 11, 2014

Related U.S. Application Data

(63) Continuation of application No. 11/449,253, filed on Jun. 7, 2006, now Pat. No. 8,758,338, which is a continuation of application No. 10/436,779, filed on May 13, 2003, now Pat. No. 7,081,114, which is a continuation-in-part of application No. 09/726,235, filed on Nov. 29, 2000, now Pat. No. 6,728,563.

(51) Int. Cl.
| | |
|---|---|
| A61B 18/12 | (2006.01) |
| A61B 18/14 | (2006.01) |
| A61B 17/00 | (2006.01) |
| A61B 18/00 | (2006.01) |

(52) U.S. Cl.
CPC .... *A61B 18/1492* (2013.01); *A61B 2017/003* (2013.01); *A61B 2017/00243* (2013.01); *A61B 2018/00184* (2013.01); *A61B 2018/00357* (2013.01); *A61B 2018/00577* (2013.01)

(58) Field of Classification Search
CPC .............. A61B 18/1492; A61B 5/6857; A61B 2017/003; A61B 2018/1432; A61B 2018/1435; A61B 5/6855; A61M 25/0147
USPC .................................................. 606/1, 41–49
See application file for complete search history.

(56) References Cited

U.S. PATENT DOCUMENTS

| | | | |
|---|---|---|---|
| 4,920,980 A | 5/1990 | Jackowski | |
| 4,960,134 A | 10/1990 | Webster, Jr. | |
| 5,125,896 A | 6/1992 | Hojeibane | |
| 5,160,233 A * | 11/1992 | McKinnis | ............... F16B 31/00 411/267 |
| RE34,502 E | 1/1994 | Webster, Jr. | |

(Continued)

*Primary Examiner* — Aaron Roane
(74) *Attorney, Agent, or Firm* — Wiley Rein LLP (57) ABSTRACT

A remotely deflectable electrophysiology/ablation catheter of the type intended for placing into an interior passage of the heart. The distal end of the catheter has a pair of tension/compression members each with a flattened end portion connected to the distal electrode and extending through the catheter casing and attached to an actuator for effecting the tension/compression thereon for remotely curling the distal end of the catheter. Spaced ring electrodes are provided adjacent the distal electrode. A permanent bend is pre-formed in the casing and tension/compression members adjacent the ring electrodes about an axis perpendicular to the elongated tension/compression members. Movement of the remote actuator causes the distal portion of the catheter to curl into a lariat in a plane perpendicular to the axis along the elongated catheter casing, thus permitting electrical mapping or ablation with the distal and/or ring electrodes.

15 Claims, 11 Drawing Sheets

(56) References Cited

U.S. PATENT DOCUMENTS

| | | | |
|---|---|---|---|
| 5,354,297 A | 10/1994 | Avitall | |
| 5,588,964 A | 12/1996 | Imran et al. | |
| 5,611,777 A | 3/1997 | Bowden et al. | |
| 5,656,029 A | 8/1997 | Imran et al. | |
| 5,673,695 A | 10/1997 | McGee et al. | |
| 5,715,817 A | 2/1998 | Stevens-Wright et al. | |
| 5,755,760 A | 5/1998 | Maguire | |
| 5,820,591 A | 10/1998 | Thompson et al. | |
| 5,861,024 A | 1/1999 | Rashidi | |
| 5,935,102 A | 8/1999 | Bowden et al. | |
| 5,938,694 A * | 8/1999 | Jaraczewski | A61B 5/0422 600/373 |
| 5,944,690 A | 8/1999 | Falwell et al. | |
| 5,951,471 A | 9/1999 | De la Rama | |
| 5,987,344 A | 11/1999 | West | |
| 6,002,955 A | 12/1999 | Willems et al. | |
| 6,183,463 B1 | 2/2001 | Webster, Jr. | |
| 6,308,090 B1 | 10/2001 | Tu et al. | |
| 6,325,797 B1 | 12/2001 | Stewart et al. | |
| 6,356,790 B1 | 3/2002 | Maguire et al. | |
| 6,413,234 B1 * | 7/2002 | Thompson | A61M 25/0136 600/434 |
| 6,514,249 B1 | 2/2003 | Maguire et al. | |
| 6,652,515 B1 | 11/2003 | Maguire et al. | |
| 6,652,517 B1 | 11/2003 | Hall et al. | |
| 7,081,114 B2 | 7/2006 | Rashidi | |

* cited by examiner

ELECTROPHYSIOLOGY/ABLATION CATHETER HAVING LARIAT CONFIGURATION OF VARIABLE RADIUS

CROSS-REFERENCE TO RELATED APPLICATIONS

This application is a continuation of U.S. application Ser. No. 11/449,253, filed 7 Jun. 2006 (the '253 application), now U.S. Pat No. 8,758,338, which is a continuation of U.S. application Ser. No. 10/436,779, filed 13 May 2003, now U.S. Pat No. 7,071,114, issued 25 Jul. 2006 (the '114 Patent), which is a continuation-in-part of U.S. application Ser. No. 09/726,235, filed 29 Nov. 2000, now U.S. Pat. No. 6,728,563, issued 27 Apr. 2004 (the '563 patent). The '253application, the '114 Patent, and the '563 Patent are all hereby incorporated by reference as though fully set forth herein.

BACKGROUND OF THE INVENTION a. Field of the Invention

The instant invention relates to an electrophysiology/ablation catheter and methods of using such catheters. In particular, the instant invention relates to electrophysiology/ablation catheters having a curvature.

b. Background Art

The present invention relates to a catheter employed for diagnostic and/or therapeutic procedures in medicine, more specifically in minimally invasive cardiac electrophysiology studies and/or cardiac ablation procedures.

Catheters of the above-described type are known in the art and, in particular, catheters capable of bi-directional curvature or lateral deflection upon movement of a remote manual actuator. A catheter of the aforesaid type employing tension/compression members without the need for a compression strut is known; and, in particular such a catheter is shown and described in commonly owned application Ser. No. 09/232,866 which is a continuation-in-part application of the disclosure of U.S. Pat. No. 5,861,024 commonly owned by the assignee of the present invention, the details of each being expressly incorporated herein by reference. The catheter described in the aforesaid '024 patent is of the type that is bi-directionally curveable in a generally planar curvature for entering the passages of the heart. In certain procedures the catheter is inserted through the femoral vein to a first chamber of the heart and it is then desired for the end of the catheter employing the electrodes to enter into another passage of the heart communicating with the first chamber of the insertion.

In addition, it has been desired to have the catheter conform to the inner periphery of certain passages in the heart and in particular the pulmonary vein for mapping or taking of electrical measurements of the condition of the inner periphery of the aforesaid passage or, in certain cases, performing ablation procedures on the passage of the heart.

Heretofore, it has been possible to deflect the catheter laterally with respect to the direction of elongation of the catheter casing; however, it has not been possible to provide such a catheter which could conform to the transverse peripheral configuration of the interior of the heart passage for which it is desired to conduct these studies and/or ablation procedures. Thus, it has been desired to find a way to map the inner periphery of the passage of the heart in a circumferential or transverse direction with a remotely inserted and remotely actuated deflectable tip catheter, and particularly one in which the radius of curvature can be minimized to provide access to other passages or passage portions that have been heretofore inaccessible.

BRIEF SUMMARY OF THE INVENTION

The present invention provides a solution to the above-described problem of utilizing a remotely insertable and deflectable tip catheter in a passage in a human heart and deflecting the distal end of the catheter in a substantially lariat configuration or curvature in a plane generally perpendicular to the direction of elongation of the catheter, and particularly reducing a radius of the lariat configuration to thereby allow the distal end to be inserted into smaller dimensioned passages or passage portions. In other words, the distal end of the catheter is curved in a planar curvature about an axis, which is parallel to the direction of elongation of the catheter casing.

The catheter of the present invention can employ tension/compression members anchored to the distal end of the catheter and which extend through the catheter casing to the proximal end and which are connected to an actuator for manually applying tension to one of the tension/compression members while compressing the other for remotely affecting the curvature of the distal end of the catheter when the catheter is inserted typically through the femoral vein into a passage in the heart.

The catheter of the present invention may have a plurality of spaced electrodes disposed on the distal end of the casing of the catheter; and, each of these electrodes may have an electrical lead connected thereto which extends through the casing to the proximal end of the catheter for external electrical connection thereto.

The catheter casing and tension/compression members may have a permanent bend or pre-formed bend of about a right angle formed adjacent the proximal-most electrode; and, this preformed bend remains in the casing as the catheter is deflected and inserted through a guide tube placed in the vein for entry into the heart passage. Upon user movement of the remote actuator, which affects movement of the tension/compression members inside the casing, the distal end of the catheter deflects laterally or curls into a lariat configuration in a plane generally at right angles to the direction of elongation of the catheter, or in other words, in a plane parallel to the axis of curvature of the preformed bend, which axis is at right angles to the direction of elongation of the catheter casing. The lariat is capable of extending in curvature through an angle of greater than 360 degrees and thus disposes the electrodes transversely or circumferentially at a single station about the major portion of inner periphery of the passage in the heart. This disposition of the electrodes enables an electrical mapping of the inner periphery of the heart passage or the performance of ablation procedures at spaced intervals about the circumference of the interior of the heart passage. Upon reversal of the remote manual actuator attached to the proximal end of the catheter casing, the lariat is uncurled to a straight configuration. The catheter may then be removed from the heart passage through the guide tube in vein, usually the femoral vein, from which it was inserted. In the preferred embodiment of the invention the initial permanent or pre-formed bend in the casing is formed at about 90 degree in catheters having the minimum radius for the curled loop and about 45 degree for catheters having a larger curled loop.

The catheter of the present invention has the permanent or pre-formed bend therein about an axis perpendicular to the direction of elongation of the catheters; and, the portion of the catheter distal the pre-formed bend is preferably manually flexed and inserted into the vein for entry into the heart passage. The pre-formed bend remains formed in the catheter. Upon user movement of the remote actuator, flexure of the catheter is facilitated in a plane normal to the direction of elongation of the catheter casing to thereby form a lariat for facilitating circular electrical mapping of the interior of the heart passage into which the lariat is situated.

The actuator is mounted relative to the tension/compression members so that enhanced curling of the catheter distal end is achieved upon movement of the actuator from its original position. The distal end varies in radius in response to actuation so that the lariat defines a curled loop having a curvature greater than 360 degrees. In this manner, the catheter can be advanced into passages or passage portions that have been previously inaccessible, and thereafter the curled loop opened to expand to the inner circumference of the passage.

The foregoing and other aspects, features, details, utilities, and advantages of the present invention will be apparent from reading the following description and claims, and from reviewing the accompanying drawings.

DETAILED DESCRIPTION OF THE INVENTION

Referring to FIGS. 1a through 1c and FIG. 2, the distal portion of the catheter is indicated generally at 10 and has a tubular flexible outer casing 3 with a distal end electrode 1 and a plurality of spaced electrodes 5 disposed thereon and preferably having an annular or ring shaped configuration. An initial permanent or pre-bend indicated generally at 12 is formed in the region adjacent the proximal-most one of the distal ring electrodes 5. In the presently preferred practiced, the pre-bend 12 is formed about the X axis and is formed to angle of about 90 degrees and preferably about 83 degrees for a casing of about 1.6 mm diameter (6 French) and for a minimum radius of 5 mm for the lariat as shown in dashed outline in FIG. 1c. In the present practice of the invention for a catheter casing 3 having a diameter of about 1.6 mm (6 French) and a lariat curled at 15 mm radius, a pre-formed bend 12 of about 45 degrees, as shown in solid outline in FIG. 1a, has been found satisfactory. Of course, other dimensions can be practiced without departing from the present invention.

Figure 1A:
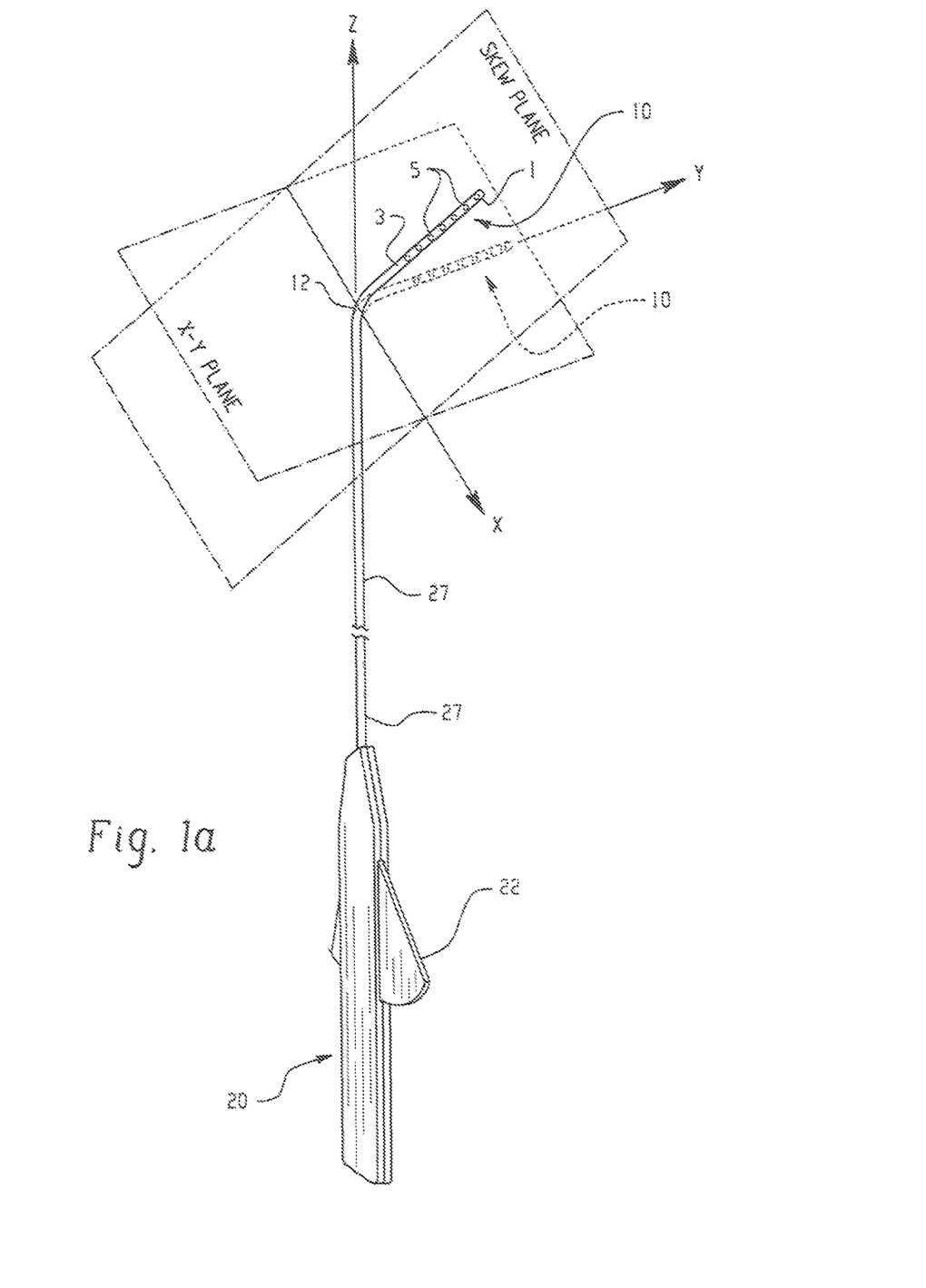
FIG. 1a is a perspective view of the distal end of the catheter of the present invention having a pre-bend formed therein.
Figure 1B:
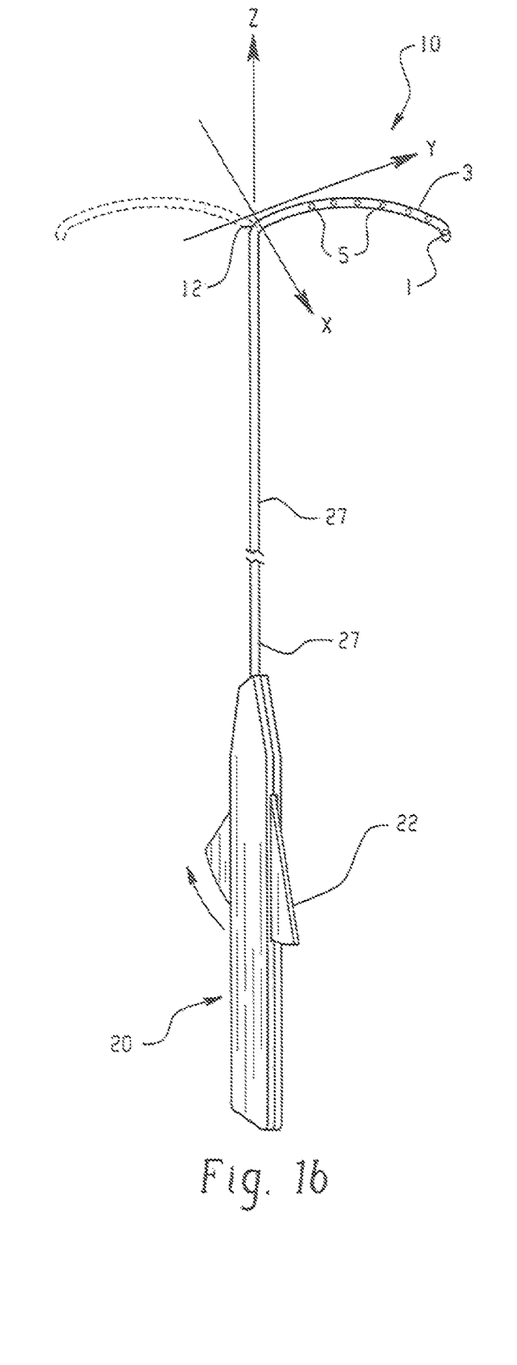
FIG. 1b is a view similar to FIG. 1a showing the distal end of the catheter partially curved by actuation from the proximal end.
Figure 1C:
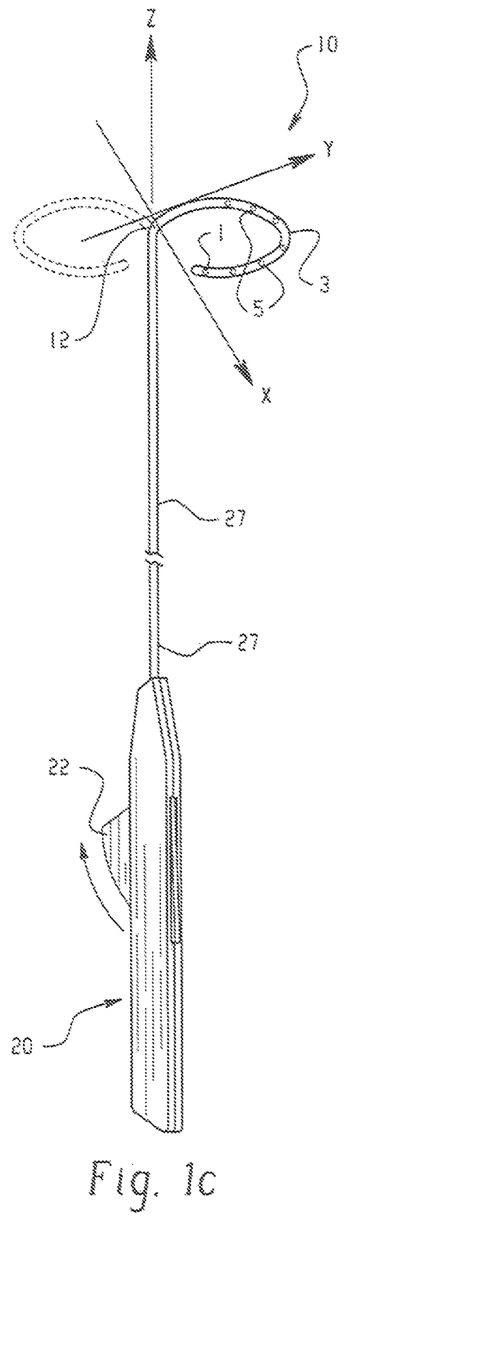
FIG. 1c is a view similar to FIG. 1b showing the catheter further deflected from the position of FIG. 1b by actuation from the proximal end to form a completed lariat of at least 270 degrees.

It will be understood that the details of actuator for the proximal end of the catheter have been omitted in FIGS. 1a through 1c for ease of illustration. However, the operation of the internal components of the catheter for affecting the flexing or curling for the lariat as shown in FIGS. 1b and 1c will be described hereinafter. In this presently preferred practice, the actuator is of the type generally shown and described in the noted commonly owned U.S. Pat. No. 5,861,024.

Figure 2:
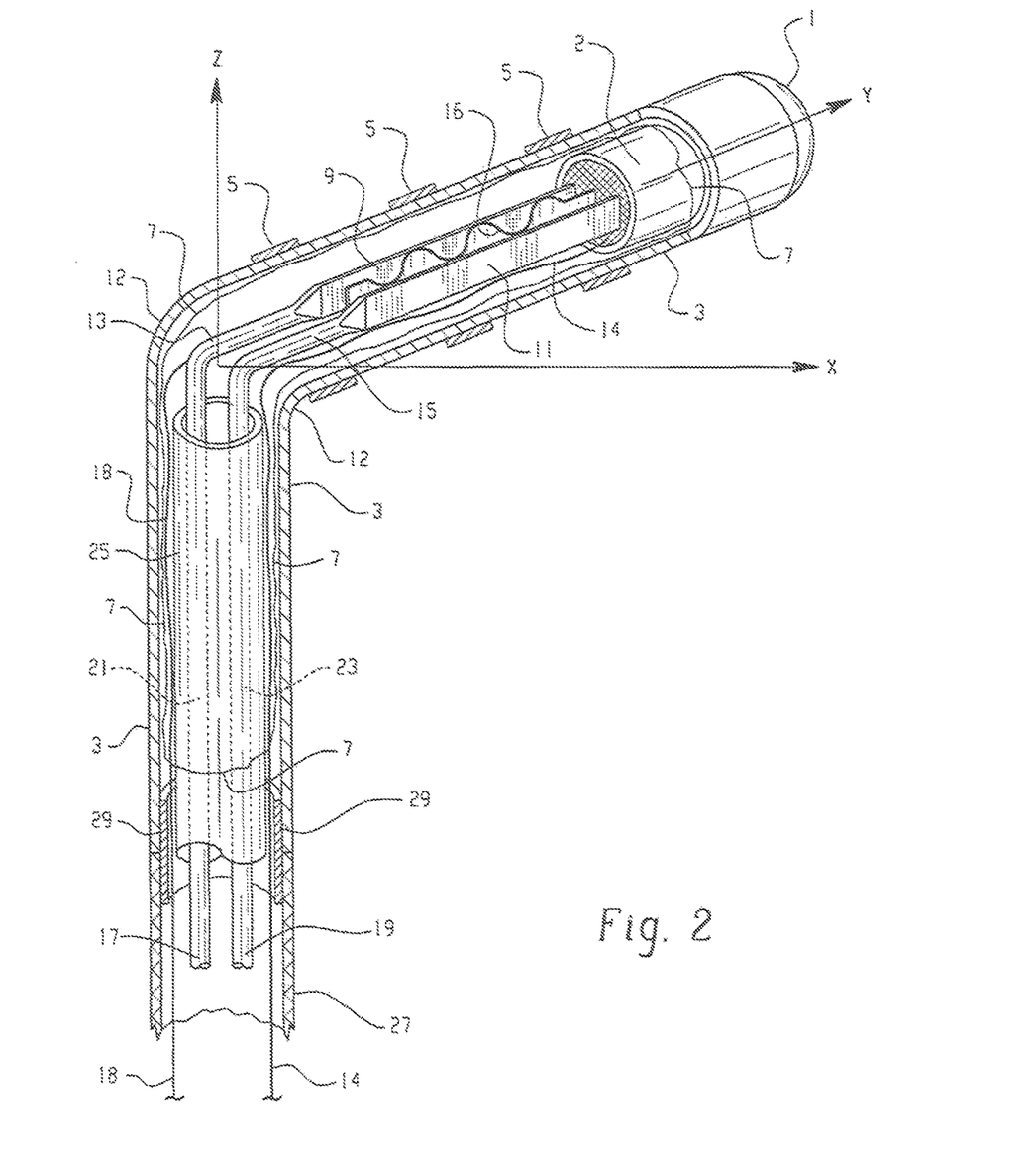
FIG. 2 is a perspective view of the distal end of the catheter after forming of the preformed bend with portions of the casing removed to show the interior components thereof.

Referring to FIG. 2, the flexible tubular casing of the catheter is shown denoted by reference numeral 3 has the ring shaped electrodes 5 disposed there over in axially spaced arrangement and spaced from the distal-most or tip electrode 1. The tip electrode 1 has a reduced diameter portion denoted by reference numeral 2 which has flattened end portions 9, 11 of the tension/compression members 13, 15 attached thereto. The portions 13, 15 have circular transverse sections, as do the portions 17, 19 extending through the casing on the opposite side of the pre-bend 12 and through the casing to the proximal end of the catheter for attachment to an actuator. The flattened ends 9, 11 of the tension/compression members 13, 15 are disposed in laterally spaced generally parallel arrangement with a resilient flexible spacer in the form of a laterally resilient wave-spring denoted by reference numeral 16 disposed therebetween.

The flattened ends 9, 11 of the tension/compression members are preferably attached to the portion 2 of the distal electrode 1 by weldment such as, for example, brazing and thereby forming a kinematic junction at the distal electrode 1 with the tension/compression members 13, 15.

The tension/compression members 13,15 have on the proximal side of the pre-bend 12 a plastic sheath or tubing 25 received thereover; and, in the present practice of the invention the tubing is formed of polyamide plastic material. However, it will be understood that alternatively other suitable plastic materials or a closely wound spring may be employed for the sheath or tubing 25.

The tip electrode 1 and each of the ring electrodes 5 has an electrical lead attached thereto which lead extends through the casing 3 to the proximal end of the catheter as denoted respectively by the electrical lead 14 for the distal electrode 1; and, a typical lead for the ring electrodes 5 is denoted by reference numeral 18.

The flattened portions of the tension/compression members 9, 11 and the portions 17, 19 in the pre-bend and the end of the tube 25 are covered with a flexible shrink tube as denoted by reference numeral 7.

A bushing 29 is received over the end of the shrink tube 7; and, the bushing 29 has attached thereto a braided sheath or exterior tube denoted by reference numeral 27. Sheath 27 has the distal end thereof abutted with casing 3; and, the opposite end extends to the proximal end of the catheter. The end of the bushing 29 opposite the braided sheath 27 on the distal end thereof is inserted within and attached to the proximal end of the non-braided casing 3.

In the present practice of the invention, the sheath or tube 25 is formed of plastic material such as polyamide plastic and extends to the proximal end of the braided exterior tube 27; however, it will be understood that the tube material is not limited to polyamide and may be formed of other suitable thermo-plastic materials or a closely wound spring which may be made from stainless steel wire, or still other suitable materials without departing from the scope and intent of the present invention.

In the present practice of the invention, it will be understood that the pre-bend 12 is permanently formed in the catheter casing and the tension/compression members 13, 15. In usage, the distal end of the catheter with electrode 1 is inserted in a guide tube placed in the patient's femoral vein; and, the portion of the catheter between electrode 1 and the pre-formed bend 12 is flexibly and temporarily resiliently flexed by the user to a position approximately parallel to that the catheter casing 3 on the proximal side of the pre-formed bend 12 so as to permit insertion of the catheter into the proximal end of a guide tube inserted in the femoral vein. It will be understood however that during this insertion of the catheter into the guide tube placed in the vein; the pre-formed bend 12 remains in its approximately right angle configuration.

Figure 4:
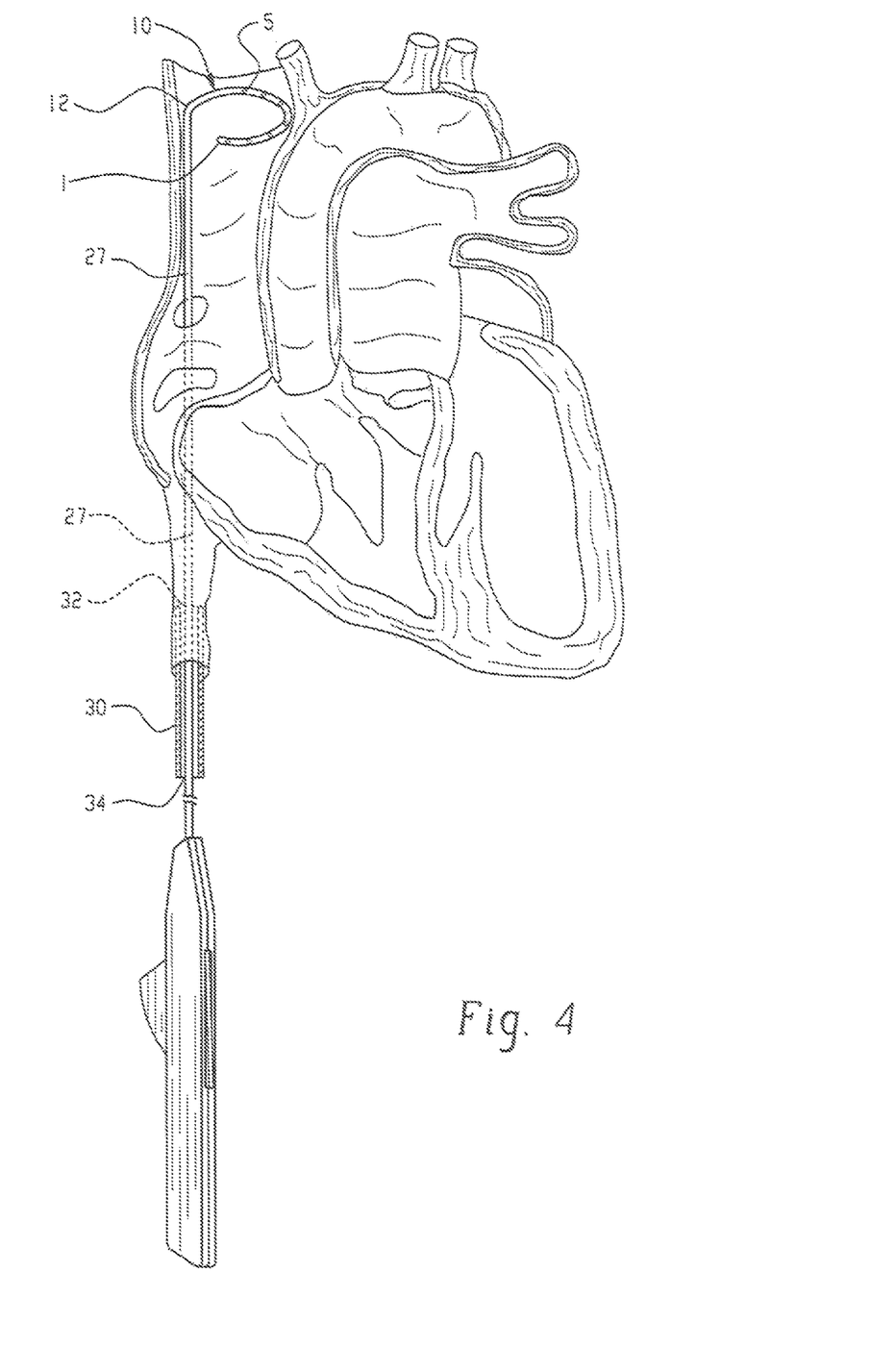
FIG. 4 is a perspective view of the heart with portion broken away to show the catheter with the lariat formed on the distal end inserted through the femoral vein into the passage within the heart.
Figure 5:
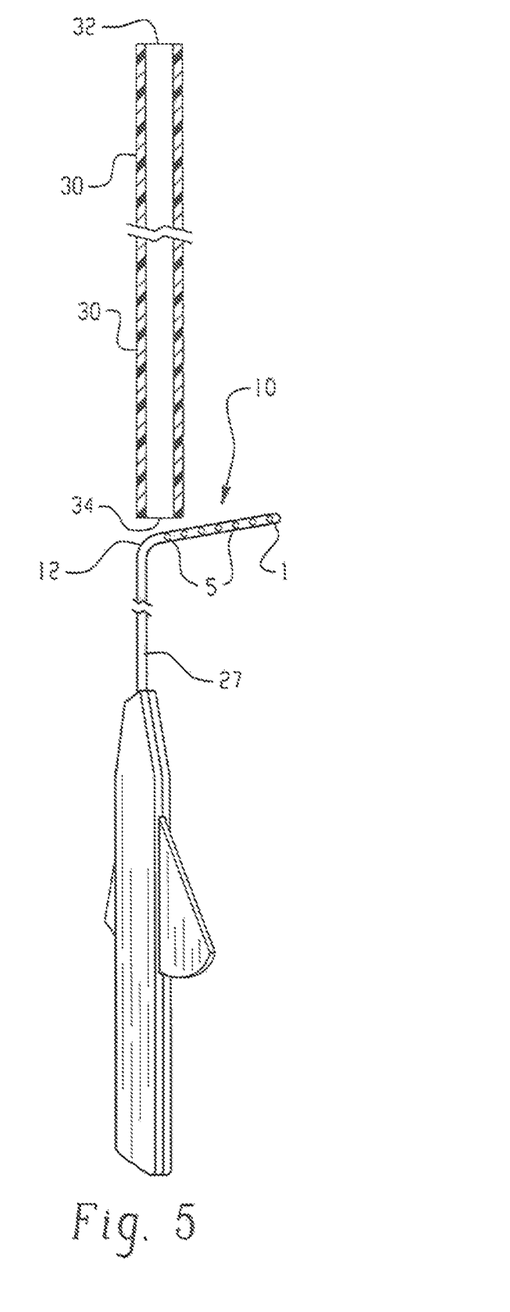
FIG. 5 is the view of the catheter of the present invention with the actuator and handle attached showing the distal end formed with the permanent bend prior to insertion in the guide tube.

Referring to FIG. 5 a guide tube is shown at 30 which is of the type insertable into the femoral vein of the patient with the distal end 32 thereof entering into the first chamber of the heart as shown in FIG. 4.

Figure 6:
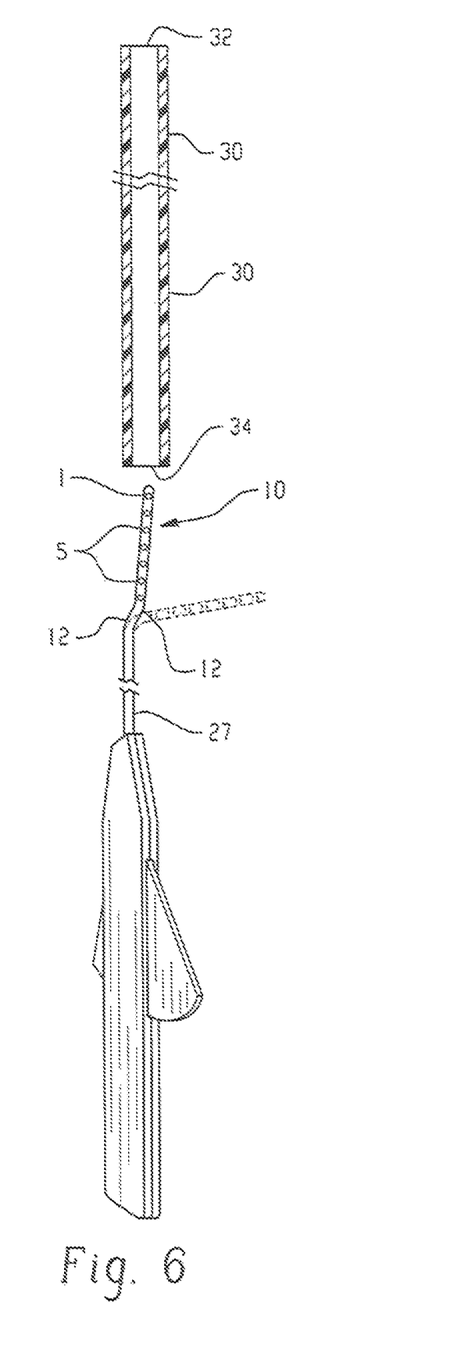
FIG. 6 is a view similar to FIG. 5 with the portion of the catheter distal end and preformed bend flexed for insertion in a guide tube.

In FIG. 6, the distal end of the catheter 10 with the preformed bend 12 therein is shown as disposed adjacent the proximal end 34 of the tube 30 prior to insertion therein.

Figure 7:
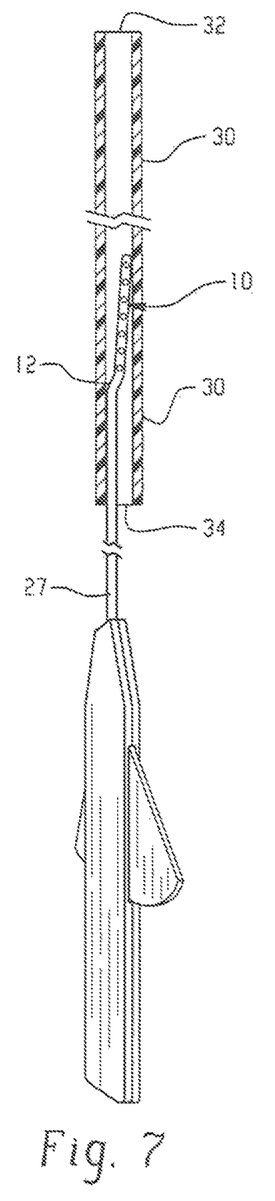
FIG. 7 is a view similar to FIG. 6 showing the distal end of the catheter of FIG. 6 inserted in the proximal end of a guide tube.
Figure 8:
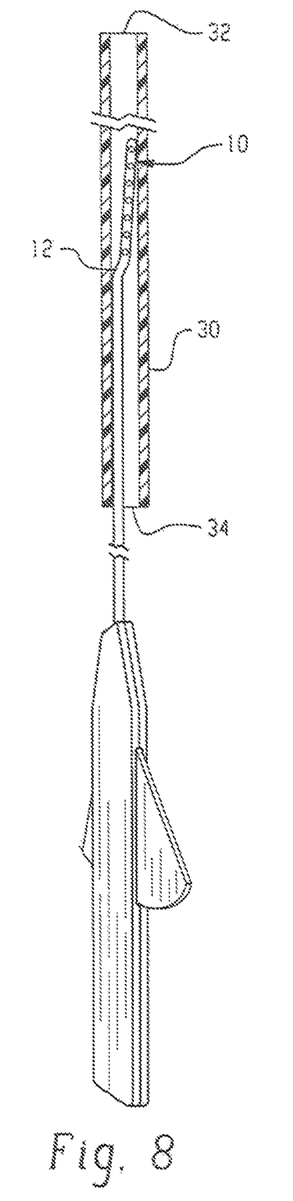
FIG. 8 is a view similar to FIG. 7 showing the distal end of the catheter further inserted into the guide tube.
Figure 9:
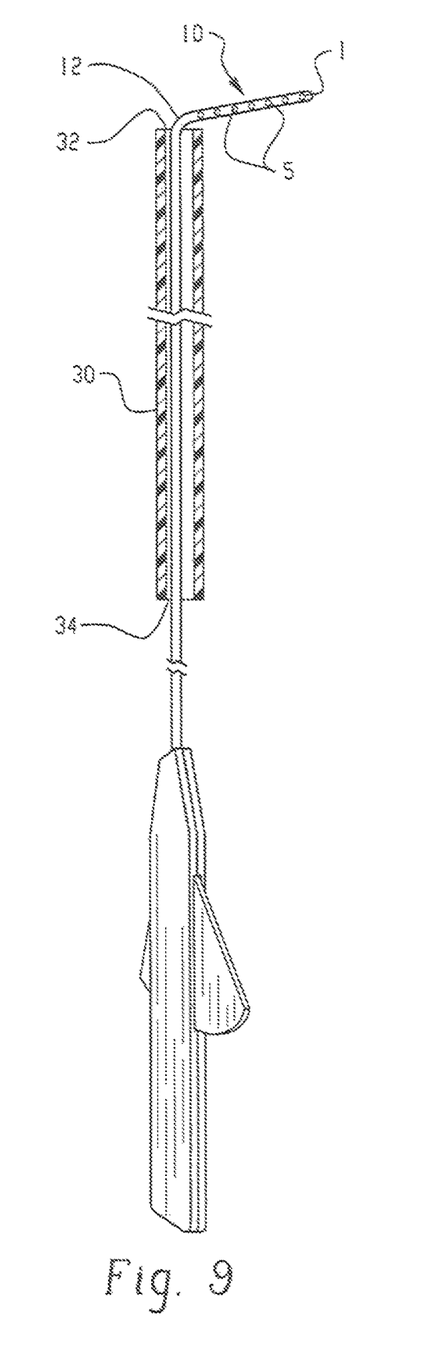
FIG. 9 is a view similar to FIG. 8 showing the distal end of the catheter including the preformed bend, extending exteriorly from the distal end of the guide tube.

In FIG. 6, the distal end 10 of the catheter is manually deformed by the user from its initial position shown in dashed outline line to the position shown in solid line outline thereby forming a substantially "S" shaped offset in the catheter about the preformed bend 12 which remains formed in the catheter. With the end 10 held in the position shown in FIG. 6, the end 10 is inserted into the proximal end 34 of tube 30 and the catheter is pushed progressively through the guide tube as shown in FIGS. 7 and 8 until the distal end 10 thereof emerges from the distal end 32 of the guide tube 30 to return to its initial condition of FIG. 5 as shown in FIG. 9 except however with the end 10 disposed within a chamber in the heart as shown in FIG. 4.

Figure 10:
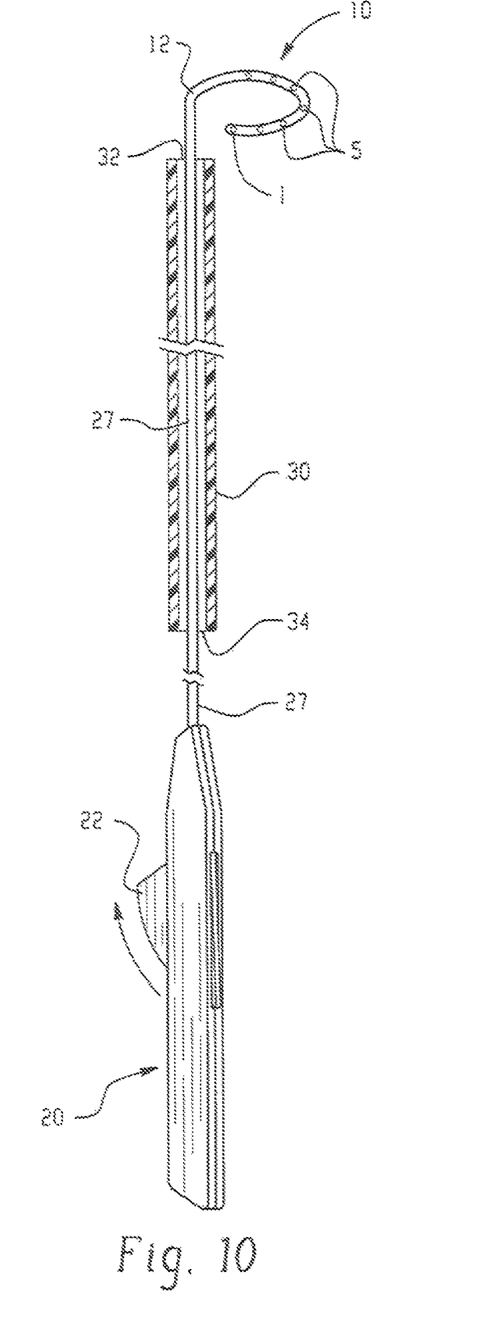
FIG. 10 is a view similar to FIG. 9 showing the distal end of the catheter curled to form a lariat in a plane at right angles to the axis of the guide tube by movement of the actuator in the direction of the arrow.

Referring to FIG. 10, the actuator indicated generally at 20 has its movable member 22 moved in the direction shown by the black arrow in the FIG. 10 to cause the flattened ends of the 9, 11 of tension/compression members to effect curling of the distal end 10 of the catheter to the lariat configuration as shown in FIG. 10 except however now within the heart chamber as shown in FIG. 4.

Formation of the curled or lariat configuration of the catheter as shown in FIG. 1c, FIG. 4, and FIG. 10 permits further placement of the catheter in the interior of the pulmonary vein of the heart for permitting either mapping of the electrical signals of the interior, or inner periphery, of the pulmonary vein or the performance of the ablation procedures by the introduction of radio-frequency electric current into the electrode 5.

Referring to FIG. 1b, the catheter is shown with the distal end partially curled by movement of the remote actuator member 22 on actuator 20.

Figure 3:
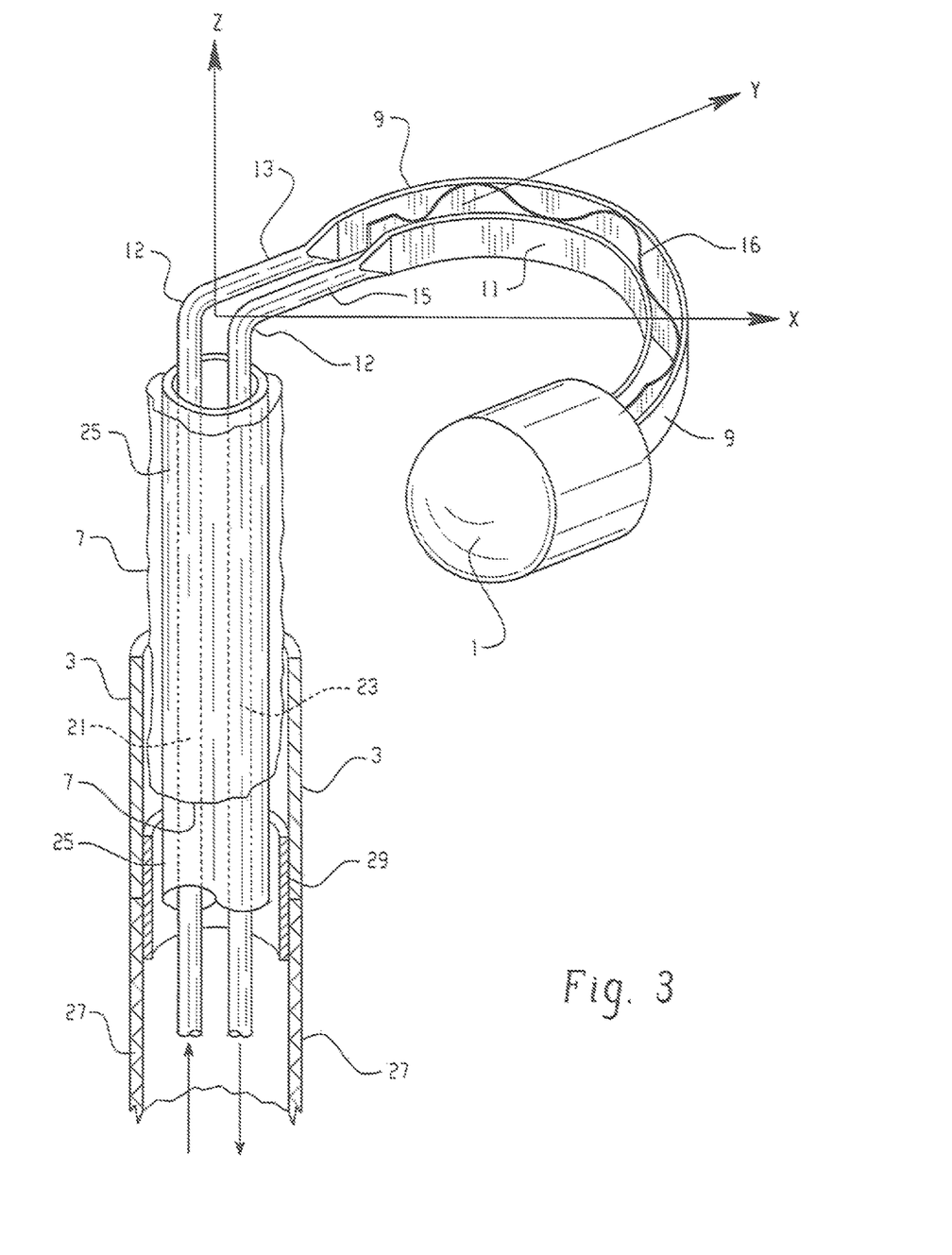
FIG. 3 is a view similar to FIG. 2 showing the distal end of the catheter, with casing removed, after actuation to form the lariat.

Referring to FIGS. 1c and 10, the catheter of the present invention is shown in the fully looped or curled into a lariat configuration of approximately 270 degrees where the pre-formed bend 12 formed about the X axis shown in FIG. 2 is retained; and, the distal portion of the catheter between distal electrode 1 and the preformed bend 12 has been flexibly curled, by the movement of the tension/compression members 17, 19, as shown by the black arrows in FIG. 1c, to cause the distal portion of the catheter to form a loop or 270 degree bend about the Z axis, or in another words forming a loop in X-Y plane with reference to the axes shown in FIG. 3. As shown in FIG. 1c, the catheter is capable of bi-directional curling by movement of the remote actuator in opposite directions.

In the present practice of the invention, the outer diameter of the catheter casing is in the same range of about 0.062 inches to 0.092 inches (1.6 mm to 2.3 mm); and, the ring electrodes 5 are spaced about 0.080 inches to 0.200 inches (2 mm to 5 mm) apart along the axis of the casing. In the present practice of the invention the catheter has accommodated 11 ring electrodes in addition to the distal electrode. Of course one skilled in the art will appreciate that the dimensions and number of electrodes are by way of example only, and the invention should not be limited to the particular examples.

In the present practice of the invention of FIGS. 1-10, a catheter having a casing diameter in the range of about 0.062 inches to 0.092 inches (1.6 mm to 2.3 mm) is capable of being curled into a lariat having an inside diameter as small as 0.400 inches (10 mm) when the catheter is flexibly deformed by movement of the manual actuator 22 to move the tension/compression members 17, 19.

Figure 11:
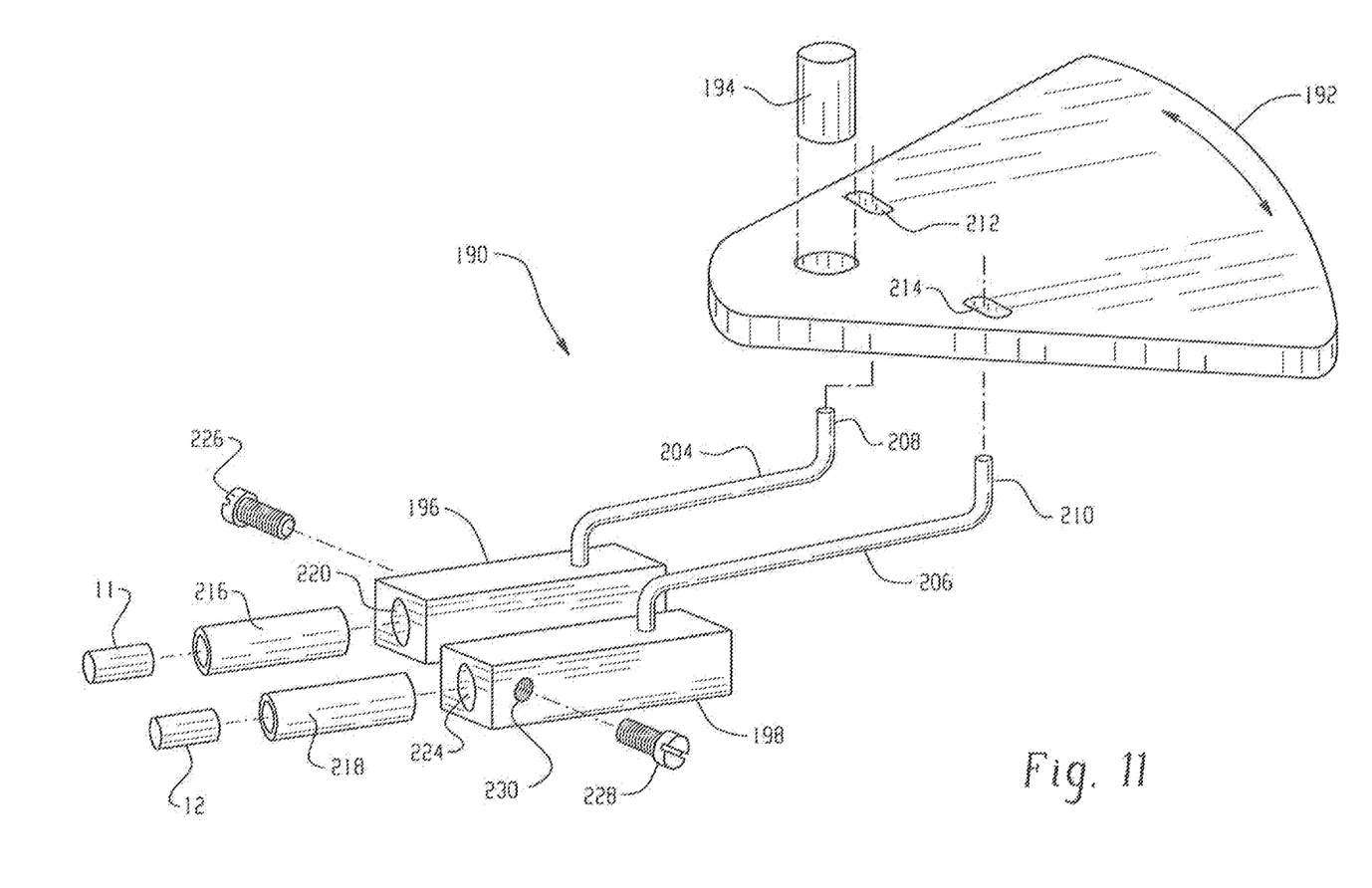
FIG. 11 is an exploded view of the catheter handle with a Scotch-Yoke mechanism for moving the tension/compression members.

Referring to FIG. 11 one of the preferred actuator embodiments as generally disclosed in the '024 patent is indicated generally at 190. The catheter handle sub-assembly 190 is shown in exploded view without the handle body with a Scotch-Yoke type pull/push mechanism for affecting formation of curvature at the distal portion of the catheter upon movement of the actuator member 192. The preferably delta shaped actuator 192 is disposed to pivot freely about pin 194 within the handle body (not shown). It will be understood that member 192 may be disposed for pivoting in a handle slot in a manner similar to actuator member 18 of FIG. 1.

Figure 12:
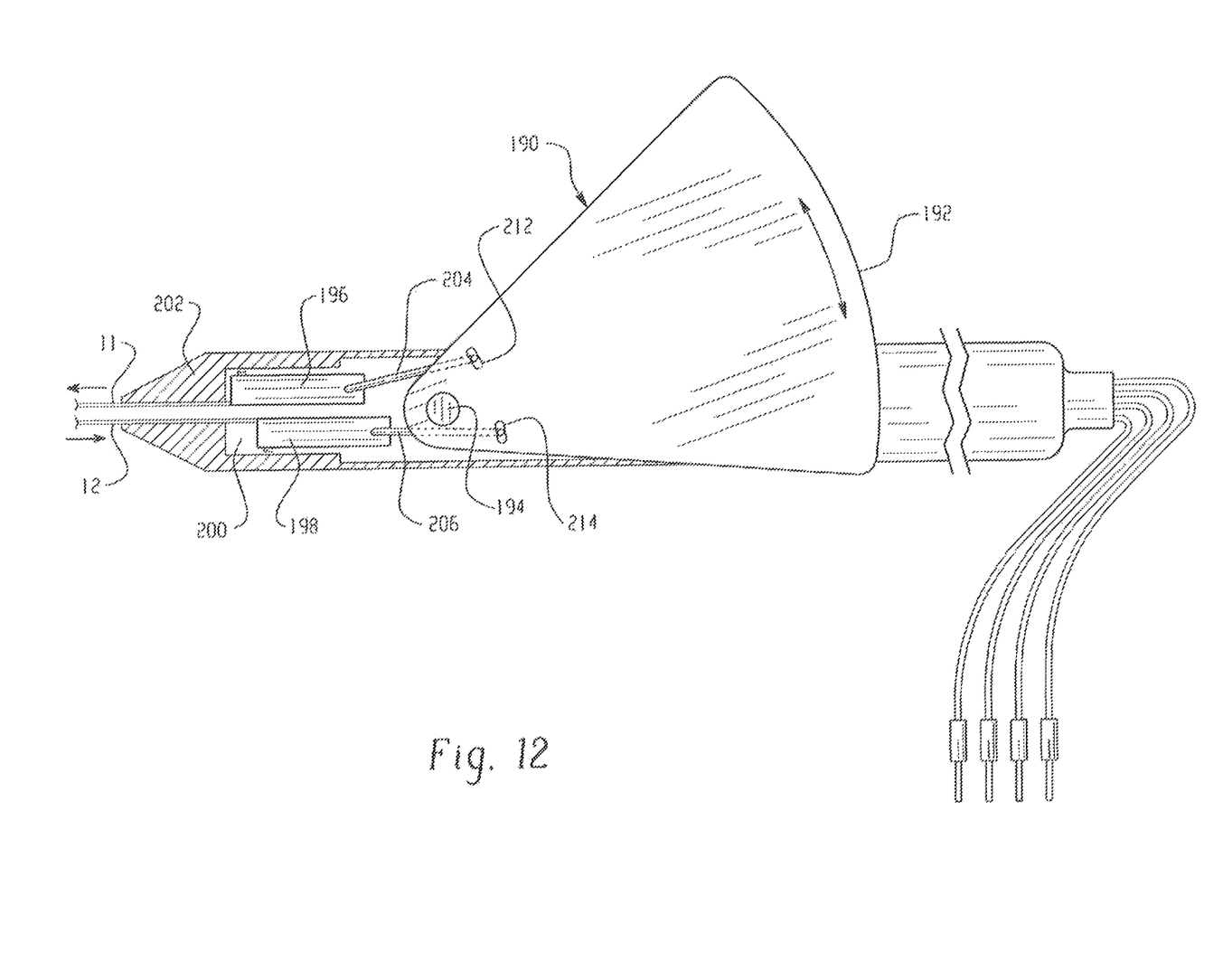
FIG. 12 is a section view of the assembled mechanism of FIG. 11 with selected portions of the housing removed for ease of illustration.

Referring to FIGS. 11 and 12, the mechanism of handle 190 comprises two symmetrically coupled sliders 196 and 198 disposed for sliding movement in groove 200 formed in handle body 202 and with the single rotating actuator 192 as the driver thereof. The sliders 196 and 198 are linked to the delta-shaped actuator 192 by non-articulating pins or links 204 and 206. Here, the links are joined to the sliders in an upper surface (as illustrated).

Referring to FIG. 11 pins or links 204, 206 are formed generally at a right angle at one end, with the ends each received in a transverse bore provided in the sliders 196, 198 with links 204, 206 extending from sliders 196, 198 outwardly in the direction of sliding movement. The opposite or free ends of links 204, 206 are also formed at right angles in a common direction orthogonal to the links-receiving bores in the sliders 196, 198 and as denoted by reference numerals 208, 210. The links 204, 206 are thus non-articulatable in a center plane passing through both sliders 196, 198.

The actuator 192 has a pair of spaced slots 212, 214 elongated in a direction transverse to delta-shaped actuator 192. Link end 208 is received in slot 212; and, link end 210 is received in slot 214. It will be understood that user movement of the actuator 192 in the direction of the block arrows in FIG. 11 will cause relative movement of the link ends into slots 212, 214 and will result in pulling one and pushing the other of the sliders 196, 198 in groove 200 of body 202.

The proximal ends of tension/compression (pull/push) members 11 and 12 are individually received in a closely fitting tubular sleeve denoted respectively 216, 218 which are in turn received individually in a longitudinal bore denoted respectively 220, 224 provided in each of the sliders 196, 198. The sleeves 216, 218 may be secured to pull/push members 11, 12 respectively by weldment if desired, as, for example by soldering or brazing. The sleeves 216, 218 and the proximal ends of members 11, 12 are secured respectively in slider bores 220, 224 by engagement with set screws torqued into threaded cross holes provided in sliders 196, 198, one such cross hole is visible in FIG. 11 at 230.

Each of the two sliders 196 and 198 slides freely, in the straight groove 200 provided in the catheter handle 202.

Referring to FIG. 12 the actuator member is shown rotated counterclockwise from the position shown in FIG. 11, wherein actuator 192 has caused rectilinear displacements of the two sliders 196 and 198 in opposite directions. Slider 196 has been moved leftward pushing member 11; and slider 198 has been moved rightward pulling member 12. This movement of sliders 196, 198 results in formation of a curvature, in a counterclockwise direction, at the distal portion of the catheter.

By orienting the actuator and sliders in a preselected offset manner, a greater range of curvature can be achieved. That is, the actuator is mounted in a nonsymmetrical manner (as opposed to the symmetrical relationship shown and described with respect to FIGS. 1-10 above) to increase the curling achieved by the lariat configuration. The actuator is intended for movement in one actuating direction through approximately twice the normal range of motion as shown in FIG. 12, thus providing approximately twice the angular movement and enhanced pushing of the slider 196. This enhanced pushing of the slider results in increased curling of the distal end of the catheter to provide a lariat that achieves curling of greater than 360 degrees, and also a reduced radius of curvature. Rather than initially locating the sliders at approximately the same axial position, one slider 196 is located ahead of the other slider 198. In this manner, actuating movement of the actuator 192 in the direction of the arrow experiences approximately twice the angular movement and the distal end of the catheter likewise undergoes enhanced curling of the lariat. This is illustrated in FIGS. 13-17.

Figure 13:
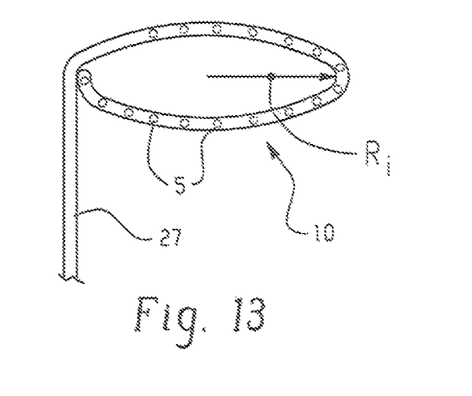
FIG. 13 is a schematic view of the catheter end actuated into a lariat configuration having a curvature of radius
Figure 14:
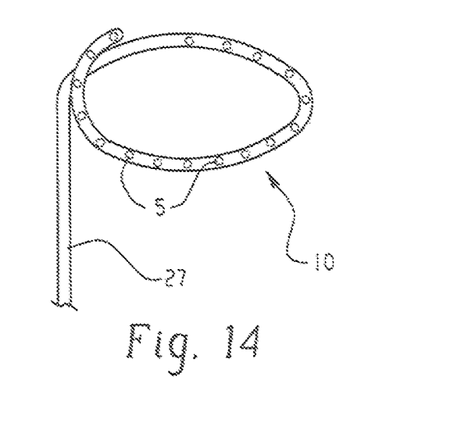
FIG. 14 is a schematic view similar to FIG. 13 in the further stages of actuated curling.
Figure 15:
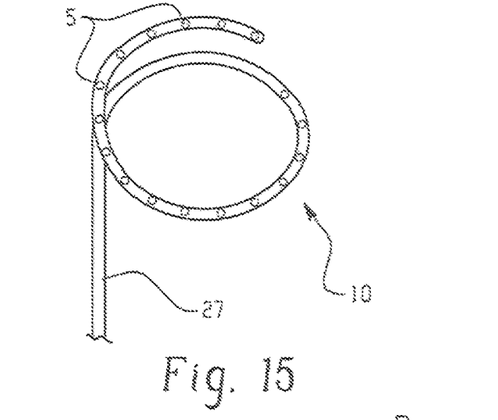
FIG. 15 is a schematic view similar to FIGS. 13 and 14 after still further actuated curling of the catheter end.
Figure 16:
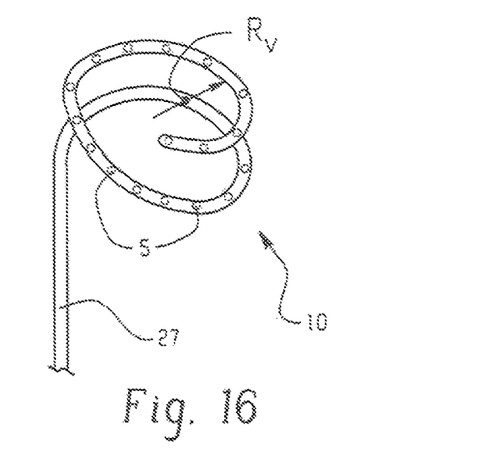
FIG. 16 is a schematic view similar to FIGS. 13-15 at full actuated curling at a curvature greater than 360 degrees of radius R.
Figure 17:
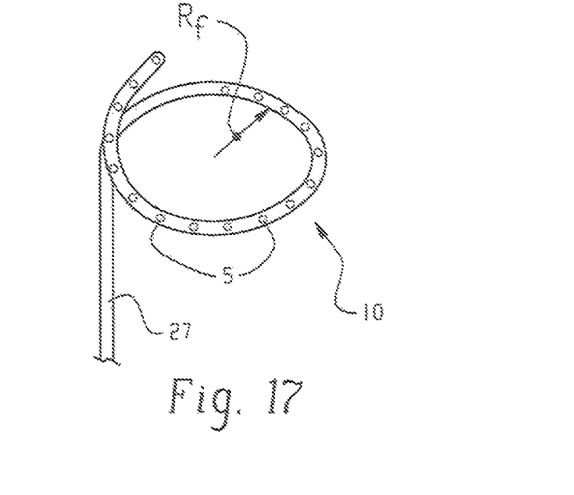
FIG. 17 is a schematic view similar to FIGS. 13-16 after opening to a final curvature $R_f$.

In FIG. 13, the actuator has been moved to achieve approximately a 360 curvature of the catheter distal end. As the actuator is further moved in the downward direction (as shown) of the arrow in FIG. 12, the slider 196 moves relative to the second slider 198, i.e., the lariat is curled to a greater extent as illustrated in FIGS. 14 and 15. As the lariat curls, the radius of curvature decreases. Thus the original curvature has a radius $R_i$ in FIG. 13 and a minimum radius $R_v$, exemplified by the lariat curvature in FIG. 16. For example, these radii can range from 25 mm to 15 mm, or similar proportional ranges. The curvature of FIG. 16 represents the maximum movement of the actuator in the direction of the arrow in FIG. 12. At this minimum radius, the lariat is more easily advanced into inner body cavities or passages such as cardiac vessels of smaller dimension than heretofore possible. Once located in the passage, the lariat is then opened (FIG. 17) to a final curvature having a radius $R_f$ that closely approximates the inner radius of the passage to be diagnosed, mapped, etc.

As will be appreciated, the initial radius $R_i$ is greater than the smallest curvature represented by the smallest radius $R_v$ in FIG. 16. It is also contemplated, however, that the final curvature radius $R_f$ is slightly greater than R. Thus, it is important that $R_v$ is less than and also that the curvature becomes greater than 360 degrees (and consequently the radius is reduced) as a result of the enhanced curling achieved by the distal end of the catheter. For example, this structure and method finds advantageous use in diagnosing, mapping, and ablating the pulmonary veins. Curling (e.g., beyond 360 degrees) of the catheter distal end is achieved by moving the actuator as inferred by the arrow in FIG. 12. This reduces the radius of curvature to a minimum radius R.

Although the invention has been described here and above with respect to the illustrated embodiments, it will be understood those skilled in the art could make numerous alterations to the disclosed embodiments without departing from the spirit or scope of this invention. For example, tension/compression members could be replaced by other actuation methods, such as one or more pull wires. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:
1. A catheter comprising:
an elongated flexible tubular body having a proximal portion and a distal portion separated by a flexible, permanent bend of at least 45 degrees;
a plurality of electrodes disposed on the distal portion of the elongated flexible tubular body; and a catheter deflection assembly comprising an actuator, wherein manual actuation of the actuator alters a curvature of the distal portion of the elongated flexible tubular body in a plane that does not include the proximal portion of the flexible tubular body by mechanically transferring a force applied to the actuator to the distal portion of the elongated flexible tubular body.

2. The catheter according to claim 1, wherein the catheter deflection assembly is operable to effect greater than a 360 degree curvature of the distal portion of the elongated flexible body.

3. The catheter according to claim 1, wherein the flexible, permanent bend is a 90 degree bend, such that the plane of the curvature of the distal portion of the elongated flexible tubular body is perpendicular to the proximal portion of the flexible tubular body.

4. The catheter according to claim 1, wherein the flexible, permanent bend is between 80 degrees and 90 degrees.

5. The catheter according to claim 1, wherein the catheter deflection assembly comprises a deflection member coupled to the actuator and extending through the elongated flexible tubular body, and wherein the force applied to the actuator is mechanically transferred to the distal portion of the elongated flexible tubular body through the deflection member.

6. The catheter according to claim 5, wherein the deflection member comprises a first, proximal portion having a circular cross-section and a second, distal portion having a flattened transverse cross-section.

7. The catheter according to claim 1, wherein the plurality of electrodes comprises a plurality of ring electrodes.

8. A catheter comprising:
an elongated flexible tubular casing having a proximal end, and at least one electrode disposed at a distal end thereof;
the elongated flexible tubular casing having a flexible, permanent bend in a distal portion of the elongated flexible tubular casing, the end forming an angle of 45 degrees to 90 degrees with respect to a longitudinal axis of the elongated flexible tubular casing;
a catheter deflection assembly disposed in the elongated flexible tubular casing, the catheter deflection assembly including a deflection member extending through the elongated flexible tubular casing, wherein the deflection member has a first portion adjacent at least the distal portion of the elongated flexible tubular casing, and a second portion adjacent at least a proximal portion of the elongated flexible tubular casing, wherein the first portion is formed to have a flattened transverse cross-section, and the second portion is formed to have a circular cross-section; and
an actuator connected to the proximal end of the catheter deflection assembly and operable upon movement to mechanically transfer a force applied to the actuator through the deflection member to the distal end to effect lateral displacement of the distal end to attain an adjustable curvature arc greater than 360 degrees when the distal portion of the elongate flexible tubular body is externally unconstrained.

9. The catheter according to claim 8, wherein the catheter deflection assembly actuates the deflection member to move the distal end in a plane normal to a longitudinal extent of the catheter.

10. The catheter according to claim 8, wherein the bend forms an angle of 80 degrees to 90 degrees.

11. The catheter according to claim 8, wherein the flattened transverse cross-section extends from the distal end to the bend.

12. The catheter according to claim 8, wherein the flattened transverse cross-section extends from the distal end through the bend.

13. The catheter according to claim 8, wherein the catheter deflection assembly comprises a pair of tension/compression members.

14. The catheter according to claim 13, further comprising a transversely resilient spacer disposed between the pair of tension/compression members.

15. The catheter according to claim 8, further comprising:
an external connection near the proximal end of the elongated flexible tubular casing; and
an electrical connection that connects the at least one electrode and the external connection.

* * * * *